(12) United States Patent
Gweon et al.

(10) Patent No.: US 7,024,925 B2
(45) Date of Patent: Apr. 11, 2006

(54) 3-AXIS STRAIGHT-LINE MOTION STAGE AND SAMPLE TEST DEVICE USING THE SAME

(75) Inventors: Dae Gab Gweon, Daejeon (KR); Dong Min Kim, Daejeon (KR); Jong Yeop Shim, Daejeon (KR); Ki Hyun Kim, Daejeon (KR)

(73) Assignee: Korea Advanced Institute of Science and Technology, (KR)

( * ) Notice: Subject to any disclaimer, the term of this patent is extended or adjusted under 35 U.S.C. 154(b) by 136 days.

(21) Appl. No.: 10/726,759

(22) Filed: Dec. 3, 2003

(65) Prior Publication Data

US 2004/0163450 A1   Aug. 26, 2004

(30) Foreign Application Priority Data

Feb. 21, 2003   (KR) ............ 10-2003-0010944

(51) Int. Cl.
*G12B 21/22* (2006.01)
*G01N 13/16* (2006.01)
*B25J 19/04* (2006.01)
*H02N 2/04* (2006.01)

(52) U.S. Cl. ............ 73/105; 250/306; 33/1 M; 33/568; 248/419; 248/542; 310/323.17

(58) Field of Classification Search .......... 73/105; 33/1 M, 568; 250/306; 248/419, 424, 542; 248/576; 269/71; 310/323.17
See application file for complete search history.

(56) References Cited

U.S. PATENT DOCUMENTS

| 4,559,717 | A |  | 12/1985 | Scire et al. ............ 33/568 |
| 4,615,591 | A |  | 10/1986 | Smith et al. ............ 359/391 |
| 4,667,415 | A |  | 5/1987 | Barsky |
| 5,281,884 | A |  | 1/1994 | Basavanhally et al. |
| 5,298,975 | A | * | 3/1994 | Khoury et al. ............ 356/624 |
| 6,229,607 | B1 | * | 5/2001 | Shirai et al. ............ 356/614 |
| 6,310,342 | B1 | * | 10/2001 | Braunstein et al. ......... 250/306 |
| 6,346,710 | B1 | * | 2/2002 | Ue ............ 250/442.11 |
| 6,467,761 | B1 |  | 10/2002 | Amatucci et al. ............ 269/58 |

FOREIGN PATENT DOCUMENTS

JP   5-232265 A   *   9/1993   ............ 33/1 M

* cited by examiner

*Primary Examiner*—Daniel S. Larkin
(74) *Attorney, Agent, or Firm*—Akerman Senterfitt

(57) ABSTRACT

A 3-axis straight-line motion stage and a sample test device using the same for supporting a predetermined sample, and comprising X-axis, Y-axis and Z-axis stages for moving the sample independently and precisely in the direction of the X-axis, the Y-axis or the Z-axis of rectangular coordinates. The 3-axis straight-line motion stage comprises a bottom plate 40 having a predetermined area and thickness; a X-axis stage 10 fixed in a reference area RR of the bottom plate 40 for moving in the direction of the X-axis a first X area RX1 positioned from the reference RR to the direction of the X-axis; a Y-axis stage 20 positioned within the first X area RX1 and fixed in a second X area RX2, which is located within the first X area RX1 for moving in the direction of the Y-axis a second Y area RY1 positioned from the second X area to the direction of the Y-axis; and a Z-axis stage 30 fixed in the second Y area RY2, which is located within the first Y area RY1 and supporting a predetermined sample for moving the sample in the direction of the Z-axis.

20 Claims, 10 Drawing Sheets

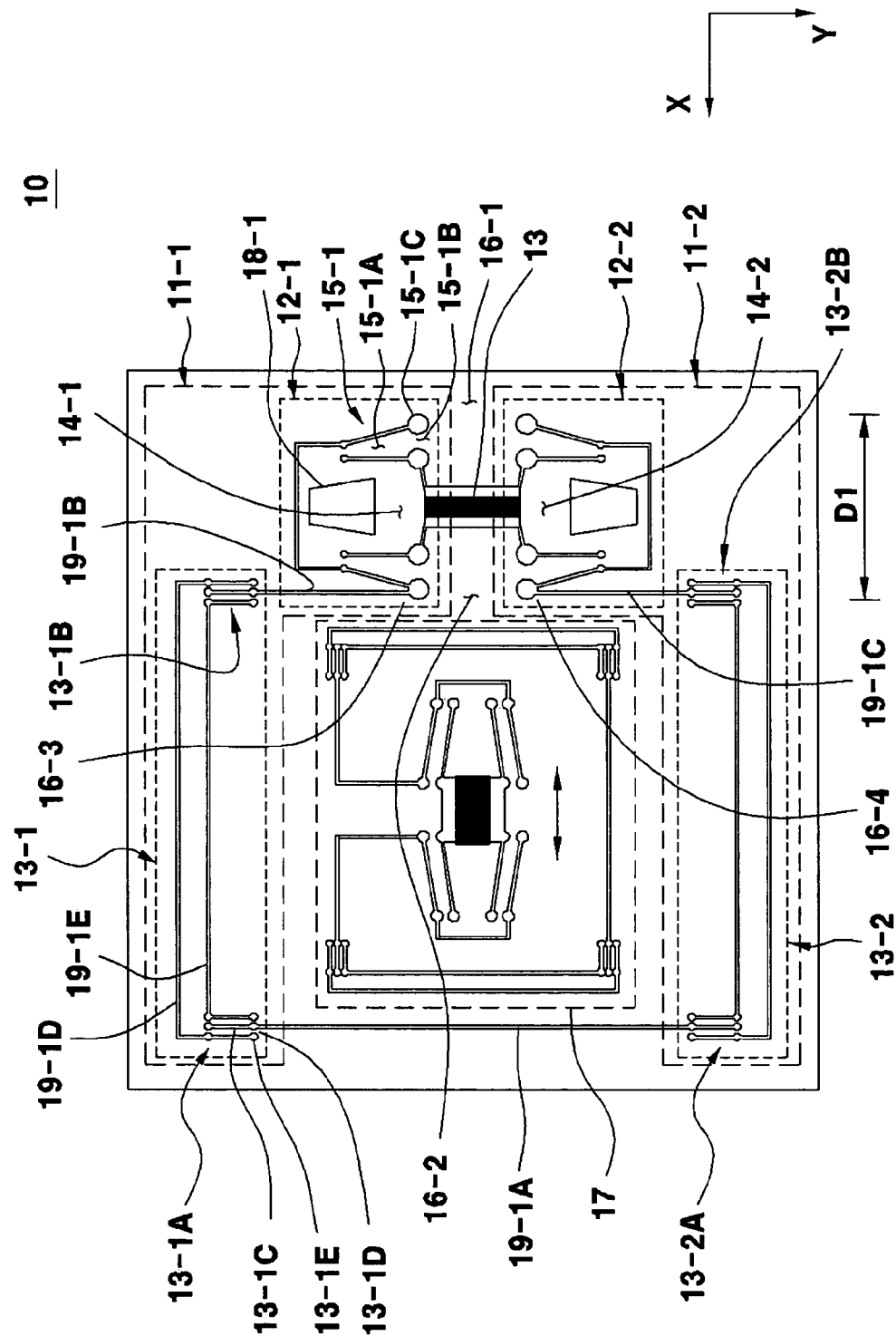

3-AXIS STRAIGHT-LINE MOTION STAGE AND SAMPLE TEST DEVICE USING THE SAME

BACKGROUND OF THE INVENTION

1. Field of the Invention

This invention relates to a 3-axis straight-line motion stage for making a 3-axis straight-line motion, and particularly relates to a 3-axis straight-line motion stage and a sample test device using the same for supporting a predetermined sample, and comprising X-axis, Y-axis and Z-axis stages for moving the sample independently and precisely in the direction of the X-axis, the Y-axis or the Z-axis of rectangular coordinates.

2. Description of the Background Art

Generally, a stage used for scanning a predetermined sample in the direction of the X-axis, the Y-axis or the Z-axis on the basis of rectangular coordinates within an atom microscope uses a piezoelectric element, such as a piezotube, and moves the sample precisely.

FIG. 1 is a constitutional view for explaining an operational principle of stage embodied using a piezotube.

The piezotube is a piezoelectric element that generates the negative and positive electric charge in proportion to the magnitude of the pressure received from the outside, whereas its length is increased or decreased in proportion to the magnitude of the voltage in case of receiving the voltage. As shown in FIG. 1, if the voltage from the electric power source is applied to the both ends of the piezotube 100, the length of the piezotube 100 is increased by $\sqcap L$ from $L_0$, which means the length before the voltage is applied, to change to $L_0 + \ulcorner L$, simultaneously the diameter in the same radial direction perpendicular to the longitudinal direction thereof is decreased by $-\sqsubset D$ from $D_0$, which means the diameter before the voltage is applied, to change to $D0 - \urcorner D$. Thus, a sample supported by the piezotube in a stage where the above cylindrical pizeotube 100 is mounted may be shifted finely in the longitudinal and radial direction thereof according to the motion of the piezotube 100.

However, since the motion to the radial direction of the X-axis and the Y-axis and the motion to the longitudinal direction of the Z-axis of the piezotube supporting the sample are mutually dependent in the stage where the piezotube is mounted, when a user manipulates the piezotube to shift the sample in the desired direction of the X-axis or the Y-axis, the sample is simultaneously shifted to the undesired direction of the Z-axis. Thus, the displacement generated due to the shift in the undesired direction of the Z-axis should be compensated.

However, since a correlation between the displacement generated form the piezotube and the direction of the displacement thereof is unclear, even if the procedure for compensating the displacement of any direction is prosecuted, another error may be included in the compensating value during the compensating procedure. Thus, there has been a problem that the prior stage using the shape and characteristic of the piezoelectric element cannot shift the sample precisely.

In order to resolve the problem of the prior stage, a straight-line motion stage for shifting the sample using the displacement of one direction (the displacement of the straight-line motion) of the piezoelectric element has been developed.

FIG. 2 is a constitutional view of the prior straight-line motion stage having a lever type flexible mechanism. The mechanism shown in FIG. 2 is consisted of a lever 90 having a predetermined length, a flexible hinge 91 being a rotation center of the lever 90 and one end thereof being fixed, and a support 94 mounted on the other end opponent to the attaching side for the flexible hinge 91 for supporting the predetermined sample.

According to the mechanism, for example, if a force 93 of a predetermined magnitude is applied to a point P1 adjacent to the rotation center O of the lever 90 so that the lever 90 is rotated at the rotation displacement T1, a point P2 of the lever, on which the support 94 is mounted, is rotated at the rotation displacement T2. Here, the rotation displacement T2 of the point P2 to the rotation displacement T1 of the point P1 is proportional to the ratio of the distance from the rotation center O to the point P1 to the distance from the rotation center O to the point P2 $\{T2=(T1)(P2)/(P1)\}$.

However, even if the piezoelectric element having a range of several to several tens $\sqsubset$ amplifies the displacement range thereof through the lever 90, since the displacement from the end of the lever 90 is generated in the circumferential direction, the sample placed in the end of the lever is not shifted completely in the straight-line direction.

Meanwhile, in order to resolve the problem of the stage having the above mechanism, a double spring stage having a double straight-line spring mounted on the lever has been developed. However, the double straight-line spring stage also does not shift the sample placed in the lever in the straight-line direction.

BRIEF SUMMARY OF THE INVENTION

Therefore, an object of the invention is to provide a 3-axis straight-line motion stage and a sample test device using the same for supporting a predetermined sample and for shifting the sample independently and precisely in the straight-line direction.

Another object of the invention is to provide a 3-axis straight-line motion stage and a sample test device using the same for supporting a predetermined sample, and comprising X-axis, Y-axis and Z-axis stages having flexible mechanisms for shifting the sample independently and precisely in the straight-line direction, respectively.

Another object of the invention is to provide a 3-axis straight-line motion stage and a sample test device using the same for supporting a predetermined sample, and comprising X-axis, Y-axis and Z-axis stages having a complex hinge and/or a symmetrical amplifier for shifting the sample independently and precisely in the straight-line direction.

To accomplish the above objects, a 3-axis straight-line motion stage of the invention comprises a bottom plate having predetermined area and thickness; a X-axis stage fixed in a reference area of the bottom plate for moving in the direction of the X-axis a first X area positioned from the reference to the direction of the X-axis; a Y-axis stage positioned within the first X area and fixed in a second X area, which is located within the first X area for moving in the direction of the Y-axis a second Y area positioned from the second X area to the direction of the Y-axis; and a Z-axis stage fixed in the second Y area, which is located within the first Y area and supporting a predetermined sample for moving the sample in the direction of the Z-axis. The X-axis, the Y-axis and the Z-axis indicate axes of rectangular coordinates, respectively.

Further, a sample test device using a 3-axis straight-line motion stage, the device comprises a 3-axis straight-line motion stage supporting a predetermined sample and shifting the sample independently, precisely and exactly in the direction of the X-axis, the Y-axis or the Z-axis; and an atom microscope provided with the 3-axis straight-line motion stage for measuring the location of the sample using a laser and for scanning the sample. The X-axis, the Y-axis and the Z-axis indicate axes of rectangular coordinates, respectively.

BRIEF DESCRIPTION OF THE SEVERAL VIEWS OF THE DRAWINGS

The above and other objects, features and advantages of the invention will be apparent from the following detailed description of the preferred embodiments of the invention in conjunction with the accompanying drawings, in which:

FIG. 4A is a constitutional view for explaining an X-axis stage in FIG. 3;

DETAILED DESCRIPTION OF THE INVENTION

Figure 1:
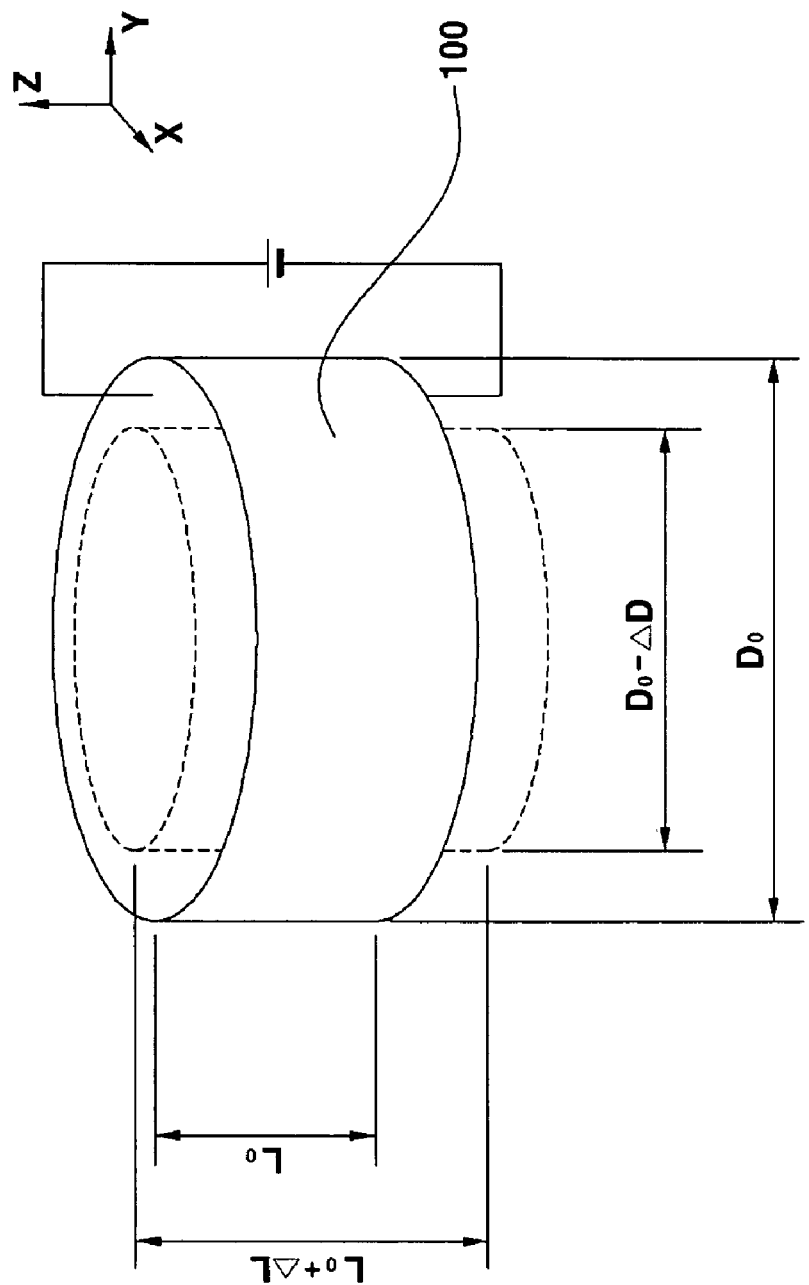
FIG. 1 is a constitutional view of the prior art 3-axis stage using a piezotube.
Figure 2:
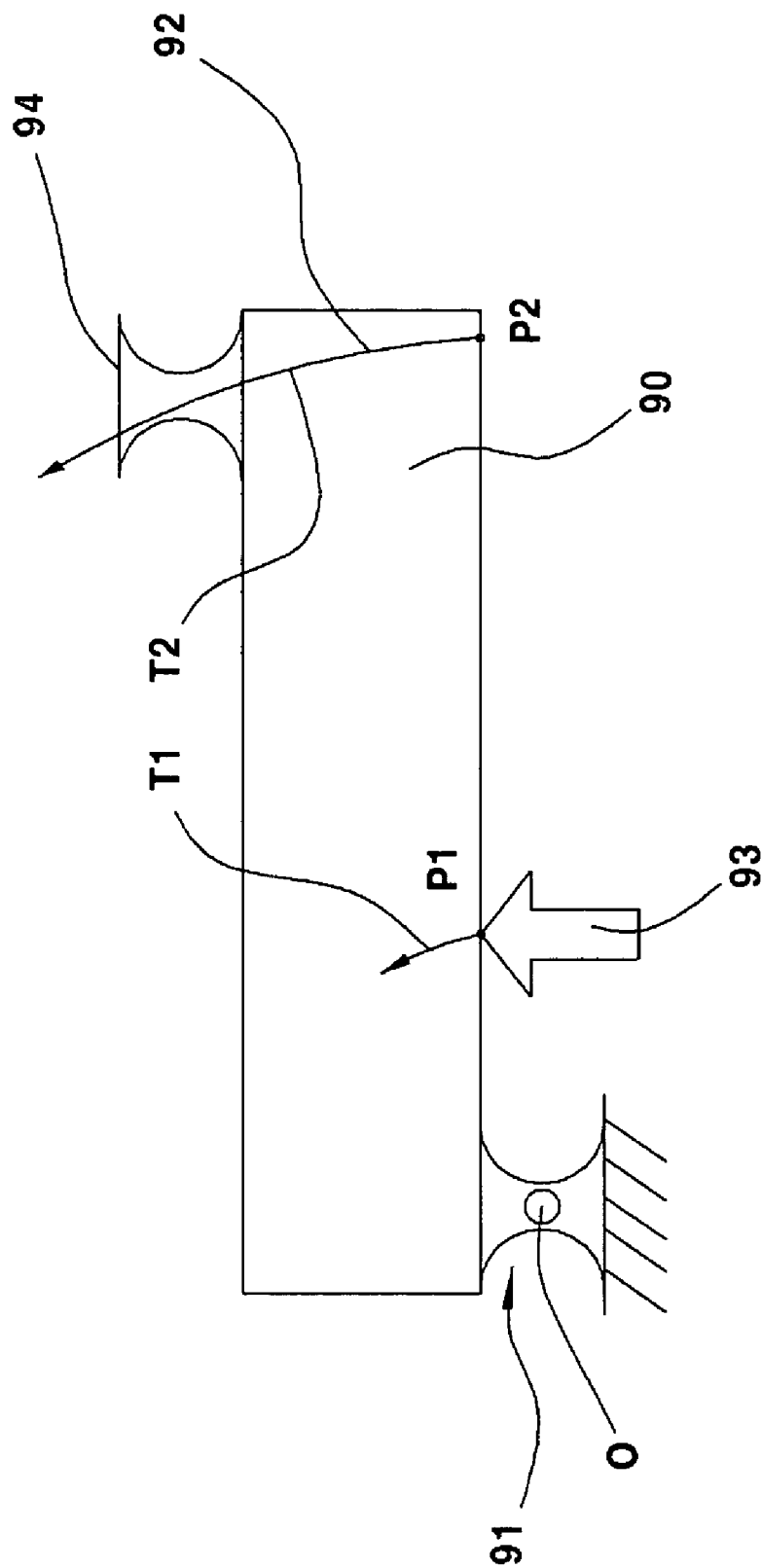
FIG. 2 is a constitutional view of the prior art straight-line motion stage having a lever type flexible mechanism.
Figure 3:
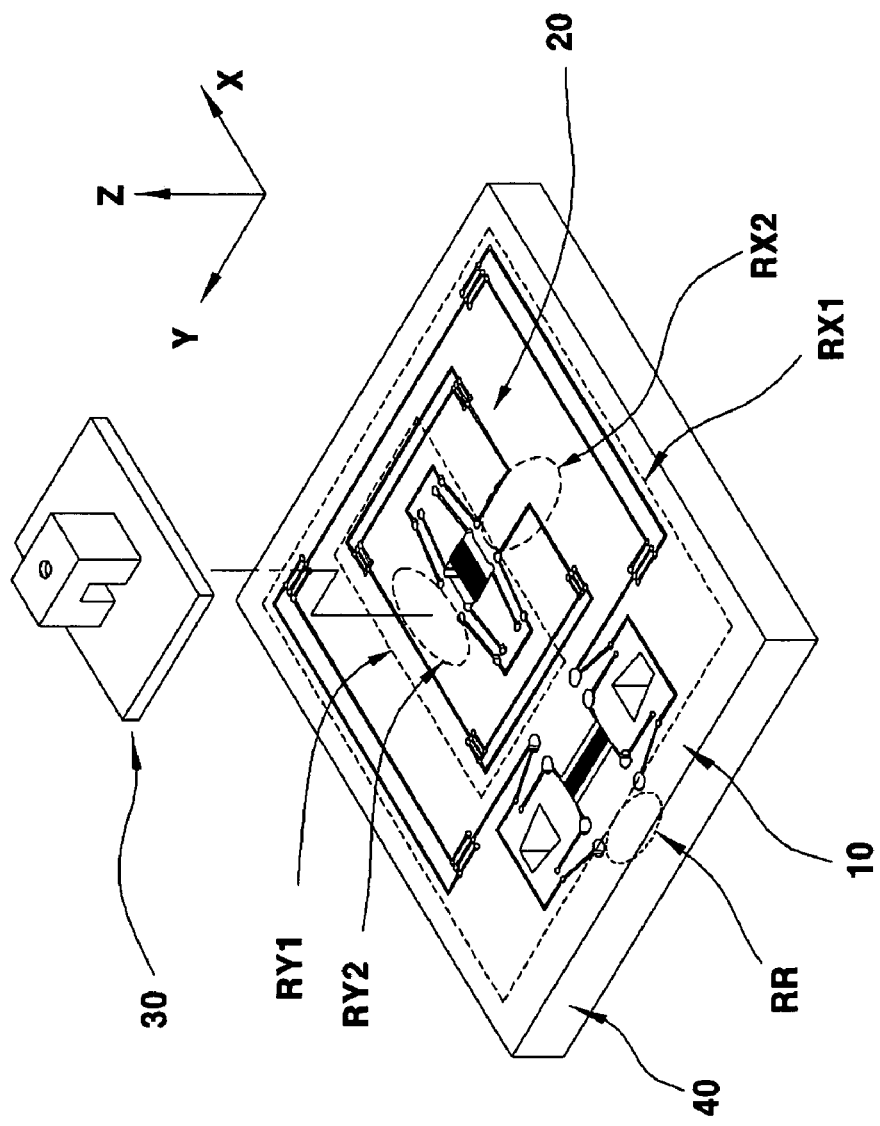
FIG. 3 is a perspective view of a 3-axis straight-line motion stage according to the invention.

FIG. 3 is a perspective view of a 3-axis straight-line motion stage according to the invention.

Referring to FIG. 3, the 3-axis straight-line motion stage comprises a bottom plate 40 having a predetermined area and thickness; a X-axis stage 10 fixed in a reference area RR of the bottom plate 40 for moving in the direction of the X-axis a first X area RX1 positioned from the reference RR to the direction of the X-axis; a Y-axis stage 20 positioned within the first X area RX1 and fixed in a second X area RX2 located within the first X area RX1 for moving in the direction of the Y-axis a first Y area RY1 positioned from the second X area to the direction of the Y-axis; and a Z-axis stage 30 fixed in the second Y area RY2 located within the first Y area RY1 and supporting a predetermined sample for moving the sample in the direction of the Z-axis. The X-axis, the Y-axis and the Z-axis indicative axes of rectangular coordinates, respectively.

Here, the first X area RX1 and the second X area RX2 mean the areas moved in the direction of the X-axis only. Further, the first Y area RY1 and the second Y area RY2 are the areas located within the first X area RX1. Even though the first Y area RY1 and the second Y area RY2 are moved in the direction only of the Y-axis in the Y-axis stage 20, the first Y area RY1 and the second Y area RY2 are finally moved to the X-axis and the Y-axis on the basis of the bottom plate 40.

Figure 4B:
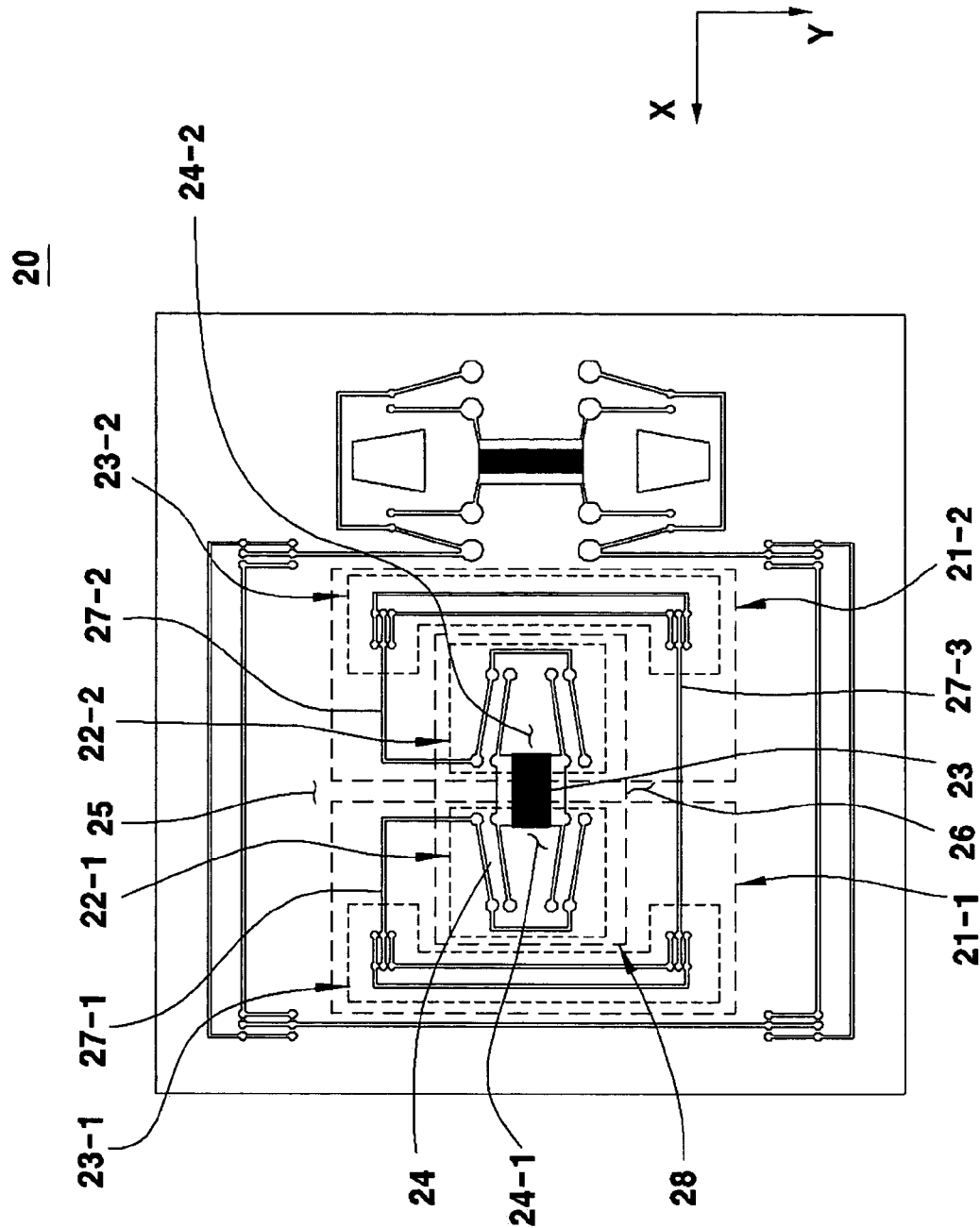
FIG. 4B is a constitutional view for explaining a Y-axis stage in FIG. 3.
Figure 4C:
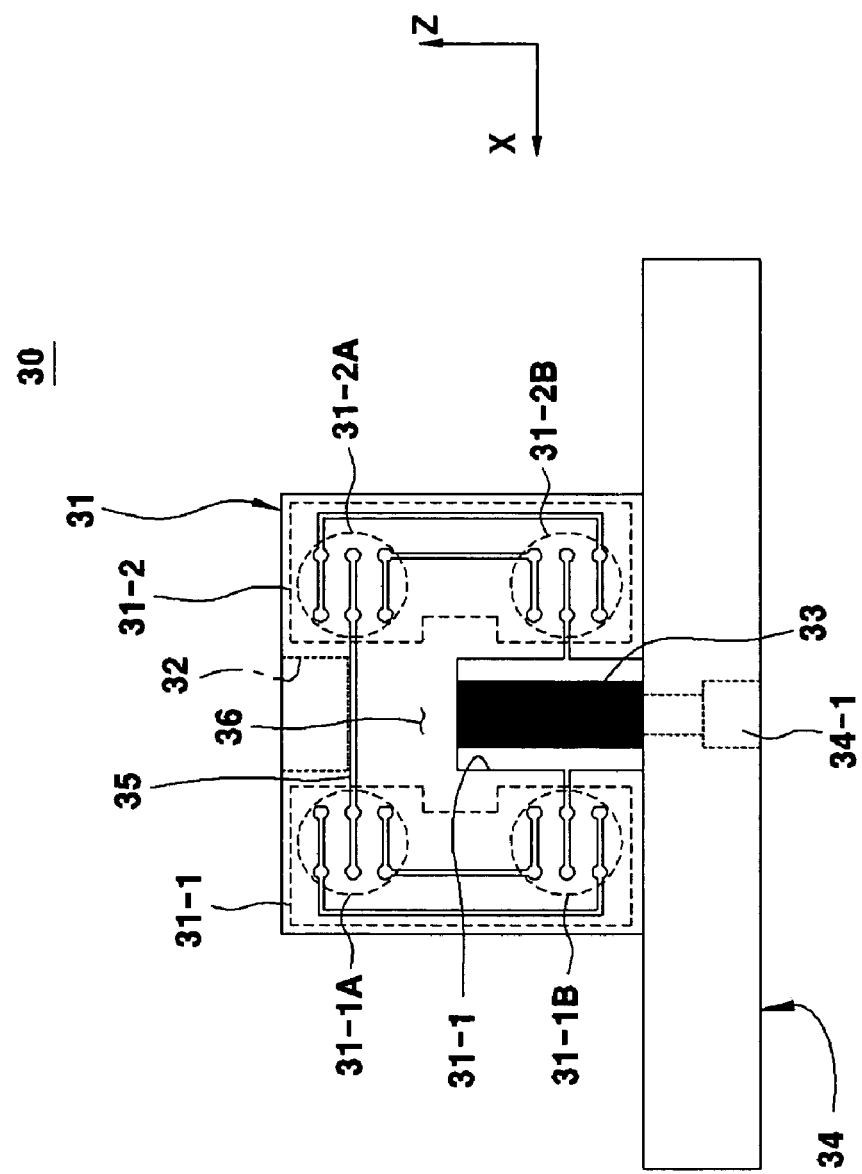
FIG. 4C is a constitutional view for explaining a Z-axis stage in FIG. 3.

With reference to FIGS. 4A to 4C, the respective stages will be described herein below.

FIG. 4A is a constitutional view for explaining the X-axis stage 10 in FIG. 3. The X-axis stage 10 comprises a piezoelectric element 13 having a predetermined length, the length being changed in the direction of the Y-axis according to an input voltage, and a first X driving part 11-1 and a second X driving part 11-2 connected to both ends of a longitudinal direction of the piezoelectric element 13, respectively, for moving in the X-axis direction the second X end 16-2 located within the first X area 11-1 from a first X end 16-1 located within the reference area RR in the center of the piezoelectric element 13 according to driving of the piezoelectric element 13.

The structures of the first X driving part 11-1 and the structure of the second X driving part 11-2 are symmetrically formed about the X-axis. Specifically, the first X driving part 11-1 and the second X driving part 11-2 connected to both ends of a longitudinal direction of the piezoelectric element 13, respectively, comprises first and second X amplifying parts 12-1, 12-2 amplifying a displacement generated according to the driving of the piezoelectric element 13 and moving third and fourth X ends 16-3, 16-4 formed in the opposite side of the first X end 16-1 in the direction of the X-axis by the amplified displacement, and first and second X-line motion parts 13-1, 13-2 connected to the third and fourth X ends 16-3, 16-4 through slits 19-1B, 19-1C, respectively, and shifted in parallel in the direction of the X-axis by the amplified displacement. Here, a slit 19-1A connects one end of the first X-line motion part 13-1, which is connected to the third X end 16-3 with one end of the second X-line motion part 13-2, which is connected to the fourth X end 16-4.

Here, the first and second X-line motion parts 13-1, 13-2, the slits 19-1A, 19-1B, 19-1C, and the second X end 16-2 form a third X area 17 having a predetermined area surrounded by themselves. The second X end 16-2 indicates a point positioned at intervals of D1 from the first X end 16-1 between the third and fourth X ends 16-3, 16-4 in the positive direction of the X-axis on the basis of the first X end 16-1.

The ends of the piezoelectric element 13 are positioned at a first pressing part 14-1 of the first amplifying part 12-1 and a second pressing part 14-2 of the second amplifying part 12-2, respectively.

Figure 5:
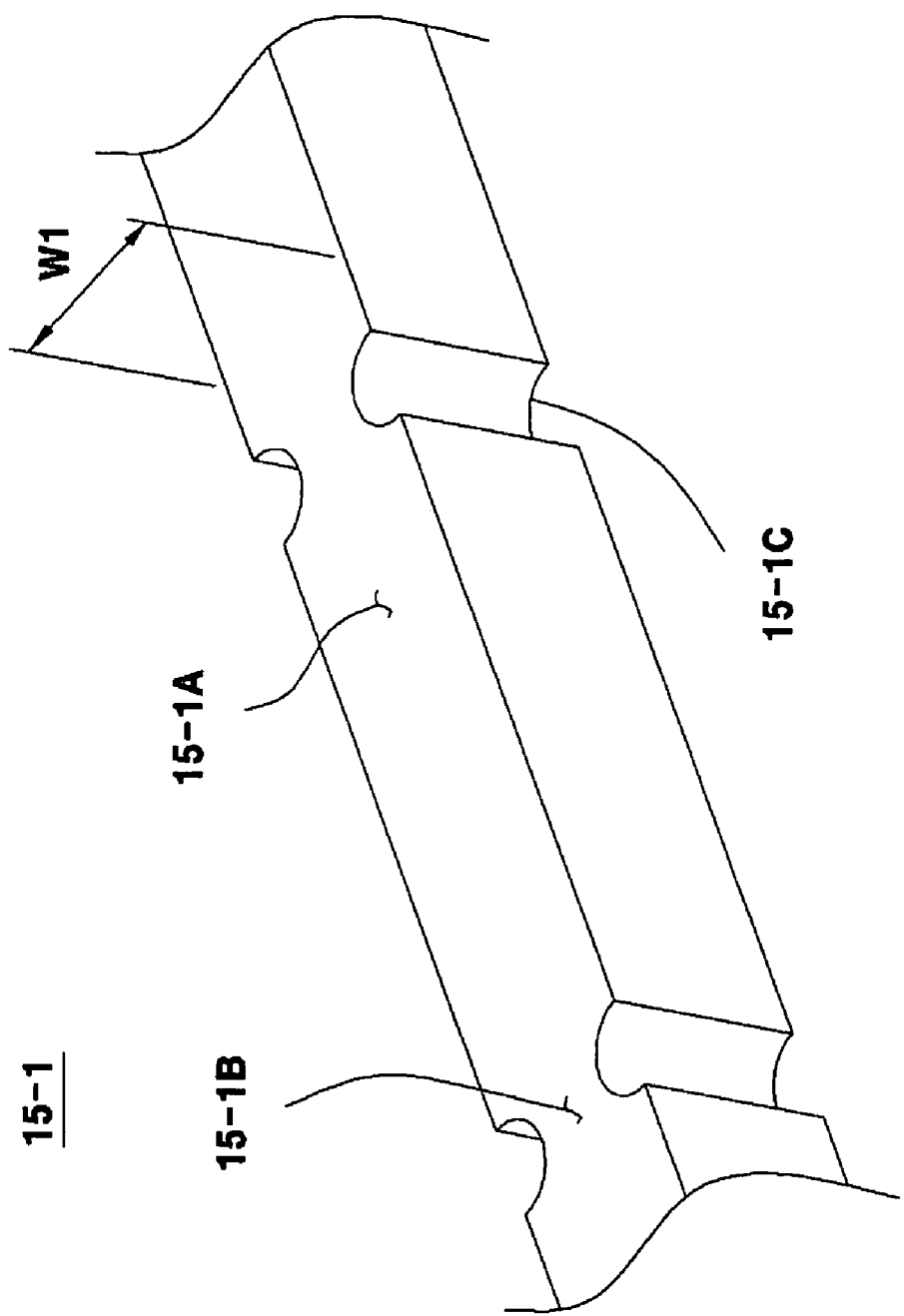
FIG. 5 is a perspective view of a middle rod of a 3-axis stage according to the invention.

The first X amplifying part 12-1 comprises the first pressing part 14-1 receiving the displacement of the piezoelectric element 13, and an intermediate rod 15-1 formed in the longitudinal direction of the piezoelectric element 13 towards both sides of the first pressing part 14-1 in the center of the first pressing part 14-1. As shown in FIG. 5, the intermediate rod 15-1 is provided with a post part 15-1A formed to have a predetermined width, and a narrowing part 15-1B having a thickness relatively narrower than the width of the post part 15-1A by a semicircular groove 15-1C having a predetermined radius in both ends of the post part 15-1A.

In the first X amplifying part 12-1, the ends (grooves) of the intermediate rod 15-1 opposite to the pressing part 14-1 about the longitudinal direction of the piezoelectric element are connected each other by a slit. Further, in order to reduce a weight of the first X amplifying part 12-1, a hole 18-1 of a predetermined magnitude may be further formed in the area surrounded by the slit, the pressing part 14-1 and the intermediate rod 15-1.

Here, a groove of the intermediate rod 15-1 is formed to give an elastic property to the intermediate rod 15-1. The narrowing part 15-1B of the intermediate rod 15-1 becomes the rotation center thereof when the post part 15-1A is rotated.

Since the second X-line motion part 13-2, which has ends 13-2A and 13-2B, has the same structure as the first X-line motion part 13-1, and they are symmetrically arranged about the X-axis, further description will be omitted.

The first X-line motion part 13-1 comprises a first X double spring 13-1B connected to the third X end 16-3 through the slit 19-1B, and a second X double spring 13-1A connected to the first X double spring 13-1B through slits 19-1D, 19-1E having a predetermined length and formed in the parallel direction about the X-axis. The second X double spring 13-1A is connected with the end 13-2A of the second X-line motion part 13-2 having the same structure as the first X-line motion parts 13-1 through the slit 19-1A.

The first and second X double springs 13-1B, 13-1A have the same structure. For example, the second X double spring 13-1A has two intermediate rods arranged doubly. The respective intermediate rod comprises a post part 13-1C having a predetermined width, which is formed in the same shape as the intermediate rod shown in FIG. 5, and a narrowing part 13-1D having a thickness relatively narrower than the width of the post part by a semicircular groove 13-1E in both ends of the post part.

Since the second X-line motion part 13-2 has the same structure as the first X-line motion part 13-1, and they are symmetrically arranged about the X-axis, further description will be omitted.

FIG. 4B is a constitutional view for explaining a Y-axis stage 20 in FIG. 3. The Y-axis stage 20 has a similar structure as the X-axis stage 10, and is formed in the third X area 17, which is located within the first X area RX1.

The Y-axis stage 20 comprises a piezoelectric element 23 having a predetermined length, the length being changed in the direction of the X-axis according to an input voltage, and a first Y driving part 21-1 and a second Y driving part 21-2 connected to both ends of a longitudinal direction of the piezoelectric element 23, respectively and fixed to the first Y end 25 of the second X area RX2 for moving the second Y end 26 opposite to the first Y end 25 in the Y-axis direction on the basis of the piezoelectric element 23. Here, although the locations of the second X area RX2 and the third area 17 are similar, the respective location will be clearly defined as shown in FIGS. 3 and 4A.

The first Y driving part 21-1 and the second Y driving part 21-2 have the same structure, and they are symmetrically arranged about the Y-axis. Specifically, the first and second Y driving parts 21-1, 21-2 comprise first and second Y amplifying parts 22-1, 22-2 connected to both ends of a longitudinal direction of the piezoelectric element 23, respectively, for amplifying a displacement generated according to the driving of the piezoelectric element 23 and for moving the second Y end 26 in the direction of the Y-axis by the amplified displacement, and first and second Y-line motion parts 23-1, 23-2 connected to the first and second Y amplifying parts 22-1, 22-2, respectively, through first and second slits 27-1, 27-2 traversing a part of the first Y end 25 and shifted in parallel in the direction of the Y-axis by the amplified displacement. Here, a slit 27-3 connects the other ends opposite to the ends of the first and second Y-line motion parts 23-1, 23-2, which are connected to the first and second amplifying parts 22-1, 22-2.

Here, the slits 27-1, 27-2, 27-3 and the first and second Y line-motion parts 23-1, 23-2 form a predetermined third Y area 28 surrounded by themselves. The first and second Y amplifying parts 22-1, 22-2 are symmetrically arranged around the Y-axis, which is located within the first Y area 28. The third Y area 28 is positioned within the first Y area RY1.

Meanwhile, the second Y end 26 indicates the position that the length of the direction of the Y-axis is increased from the end points of the first and second Y amplifying parts in the direction of the Y-axis on the basis of the first Y end 25. The first Y amplifying part 22-1 and the second Y amplifying part 22-2 have the same structure, and they are symmetrically formed about the Y-axis.

The respective first and second Y amplifying parts 22-1, 22-2, like the structures of the first and second X amplifying parts 12-1, 12-2, comprise first and second pressing parts 24-1, 24-2 receiving the displacement of the piezoelectric element 23, and an intermediate rod formed in both sides of the first and second pressing parts 14-1, 14-2 symmetrical to the X-axis in the center of the respective first and second pressing parts 14-1, 14-2.

Here, the intermediate rod 24, as shown in FIG. 5, is provided with a post part having a predetermined width W1, and a narrowing part having a thickness relatively narrower than the width of the post part by a semicircular groove having a predetermined radius in both ends of the post part. The intermediate rod 24 has the same function and operating method as the intermediate rod 15-1A of the X-axis stage.

Meanwhile, the first and second Y-axis motion parts 23-1, 23-2 have the same structure and operating principle as the first and second X-line motion parts 13-1, 13-2, and they are symmetrically formed about the Y-axis.

FIG. 4C is a constitutional view for explaining a Z-axis stage in FIG. 3. The Z-axis stage comprises a bottom part 34 having a predetermined area and thickness and fixed within the second Y area RY2 of the Y-axis stage 20, a Z-line driving part 31 moving in the direction of the Z-axis and formed integrally to the bottom plate 34 in the vertical direction, which is the direction of the Z-axis, from the surface of the bottom plate 34, and a piezoelectric element 33 mounted to have a decreased or increased length in the direction of the Z-axis in a space 31-1 of a predetermined size. The space 31-1 is formed in the Z-line driving part 31 in a region to which the bottom plate 34 and the Z-line driving part 31 are adjacent.

Here, the piezoelectric element 33 is fixed within the space 31-1 to be operated in the center of the Z-line driving part 31 by a bolt-nut joining means 34-1 formed in the bottom part 34.

The Z-line driving part 31 comprises first and second Z-axis motion parts 31-1, 31-2 moving the first Z end 36 positioned in the direction of the Z-axis from the bottom part 34 to the Z-axis according to the driving of the piezoelectric element 33, and a support receiving part 32 for supporting a sample support, which is not shown in the drawings, adjacent to the first Z end 36.

The first and second Z-axis motion parts 31-1, 31-2 have the same structure and operating principle as the first and second X-line motion parts 13-1, 13-2 or the first and second Y-line motion parts 23-1, 23-2, and they are symmetrically arranged about the Z-axis. Specifically, the respective first and second Z-axis motion parts 31-1, 31-2 include the first to fourth Z double springs 31-1A, 31-1B, 31-2A, 31-2B, and slits connecting each of them. Specifically, the first and third Z double springs 31-1A, 31-2A are connected through a slit 35.

Meanwhile, since the bottom part 34 of the Z-axis stage 30 serves to make a force generated from the piezoelectric element spread broadly across the second Y area RY2, in case that the area is larger than the second Y area RY2, a spacer, which is not shown in drawings, having a predetermined thickness may be mounted between the second Y area RY2 and the bottom part 34. Therefore, the spacer prevents the bottom part separated from the second Y area RY2 from facially contacting with, for example, the first and second Y amplifying parts of the Y-axis stage.

The amplification principle of the 3-axis straight-line motion stage of the invention and the operation method thereof will be given herein below.

Figure 6B:
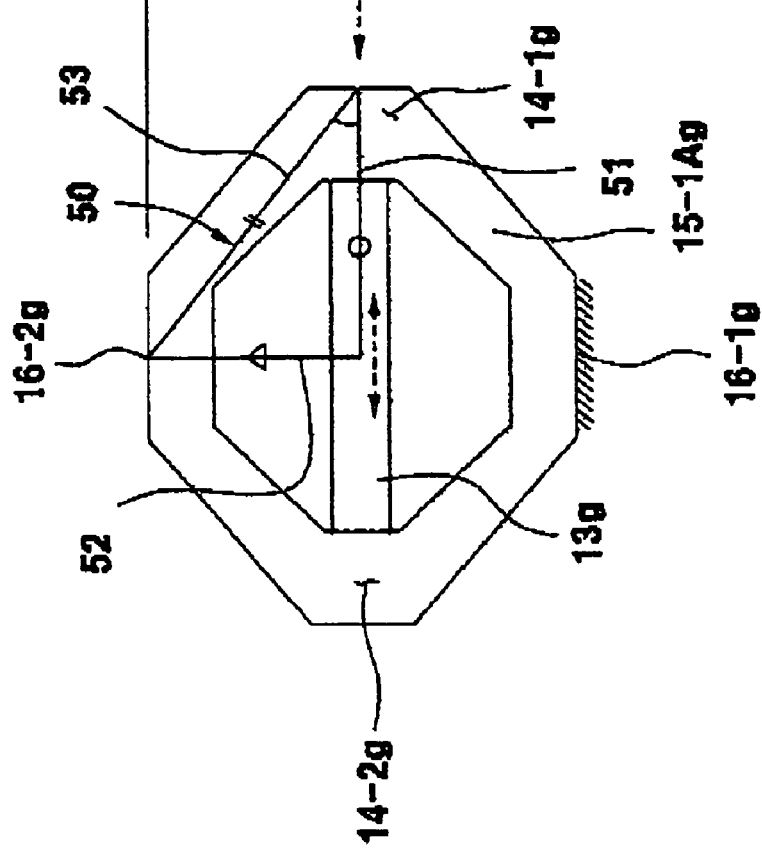
FIGS. 6A and 6B are constitutional views for explaining an amplification principle of a 3-axis straight-line motion stage according to the invention.
Figure 6A:
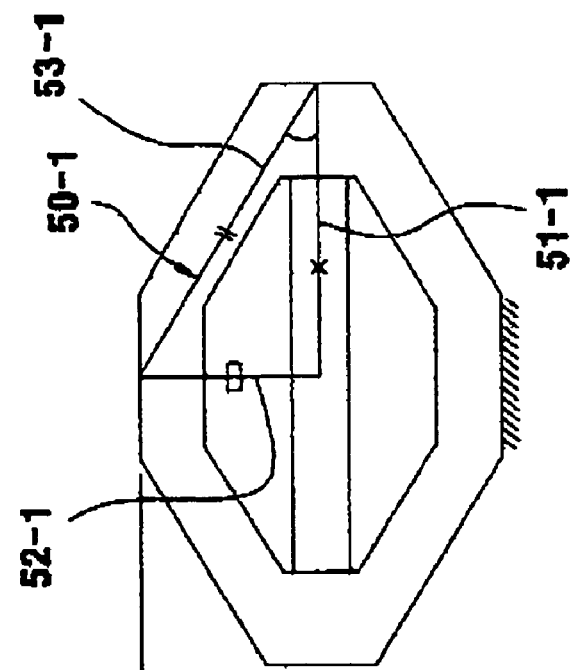

FIGS. 6A and 6B are constitutional views of models for explaining an amplification principle of a 3-axis straight-line motion stage according to the invention. For example, there are models for the first and second amplifying parts 12-1, 12-2 of the stage 10. Specifically, FIG. 6A is a constitutional view of the model for the X-axis stage when the amplifying state is in the normal state, and FIG. 6B is a constitutional view of the model for the X-axis stage when the length of the piezoelectric element of the amplifying part is increased.

Referring to FIGS. 6A and 6B, the piezoelectric element 13 corresponds to a model piezoelectric element 13g, the first and second pressing parts 14-1, 14-2 correspond to first and second model pressing parts 14-1g, 14-2g, the first and second X ends 16-1, 16-2 correspond to first and second model X ends 16-1g, 16-2g, and the intermediate rod 15-1 corresponds to a model intermediate rod 15-1Ag.

When the above elements are defined as the model elements in the models, a distance 51 between the first pressing part 14-1g and the model piezoelectric element 13g, a distance 52 between the model piezoelectric element 13g and the second model X end 16-2g, and a distance 53 between the first pressing part 14-1g and the second model X end 16-2g are defined by the distances of the base line, height and hypotenuse of a triangle 50, respectively.

Now, in case that the length of the piezoelectric element 13 is increased by the operation of the piezoelectric element 13, with a reference to FIGS. 6A and 6B, the procedure for generating the displacement of the second X end 16-2 by the operation of the first and second amplifying parts 12-1, 12-2 will be given herein below.

Since the length of the intermediate rod 15-1 is constant and the first X end 16-1 is fixed to the bottom plate 40, in case that the length of the piezoelectric element 13 is increased, the model in FIG. 6A is changed into the model in FIG. 6B. Specifically, the triangle 50 having the three lines 51, 52, 53 in FIG. 6A is changed into the transformed triangle 50-1 having the three lines 51-1, 52-1, 53-1 in FIG. 6B. Here, since the length of the intermediate rod 15-1 is constant, while the distance of the hypotenuse corresponding to the length of the intermediate rod 15-1 is not changed, the height 52 is changed into the decreased heights 52-1, and the base line 51 is changed into the increased base line 51-1. Thus, if the length of the piezoelectric element 13 is increased, the second model X end 16-2g is decreased by $\Delta x$ from the original position.

Figure 7:
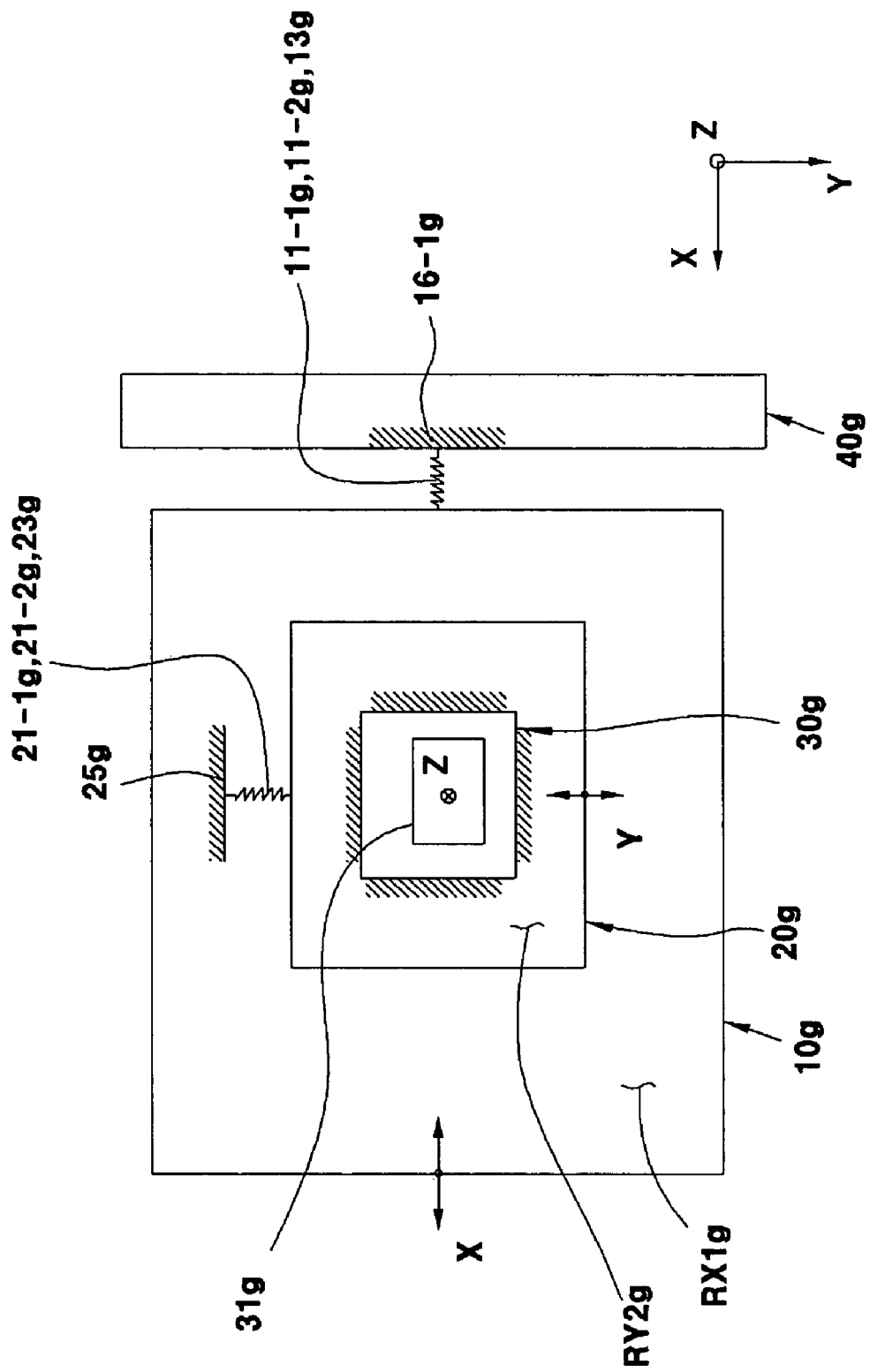
FIG. 7 is a constitutional view for explaining an operating method of 3-axis straight-line motion stage according to the invention.

FIG. 7 is a constitutional view for explaining an operating method of the 3-axis straight-line motion stage according to the invention.

Referring to FIG. 7, the bottom plate 40 corresponds to a model bottom plate 40g, the X-axis stage 10 corresponds to a model X-axis stage 10g, the Y-axis stage 20 corresponds to a model Y-axis stage 20g, the Z-axis stage 30 corresponds to a model Z-axis stage 30g, and the Z-axis motion part 31 corresponds to a model Z-axis motion part 31g. Further, the first and second X amplifying parts 11-1, 11-2 correspond to first and second model X amplifying parts 11-1g, 11-2g, and the first and second Y amplifying parts 21-1, 21-2 correspond to first and second model Y amplifying parts 21-1g, 21-2g.

Here, the Y-axis stage 20 formed in the first X area RX1 (substantially, the third X area 17) is, as shown in FIG. 7, arranged in the first model X1 and RX1g. Further, even if the area of the bottom plate of the Z-axis stage 30 is larger than that of the second Y area RY2, since the spacer prevents the Z-axis stage 30 from facially contacting the area except for the second Y area RY2, the Z-axis stage 30 is arranged in the second model Y area RY2g.

Thus, according to the operation of the piezoelectric element 13g, the first model X area RX1g of the model X-axis stage 10g is shifted in the direction of the X-axis only about the first model X end 16-1g fixed to the model bottom plate 40g. Then, the model Y-axis stage 20g arranged within the first model X area RX1g is also shifted in the direction of the X-axis only.

Meanwhile, with the piezoelectric element 23g operated in the model Y-axis stage 20g arranged within the first model X area RX1g, the second model Y area RY2g of the model Y-axis stage 20g is shifted in the direction of the Y-axis only. Specifically, since the model bottom plate 34g of the Z-axis stage 30g is fixed to only the second model Y area RY2g, the model Z-axis motion part 31g mounted on the model bottom plate 34g is shifted to the Z-axis.

Therefore, the sample support carrying the sample is shifted in only the direction of the X-axis by the model X-axis stage 10g, and is shifted in only the direction of the Y-axis by the model Y-axis stage 20g. Further, the sample support carrying the sample is shifted in only the direction of the Z-axis by the model Z-axis motion part 31g.

Figure 8:
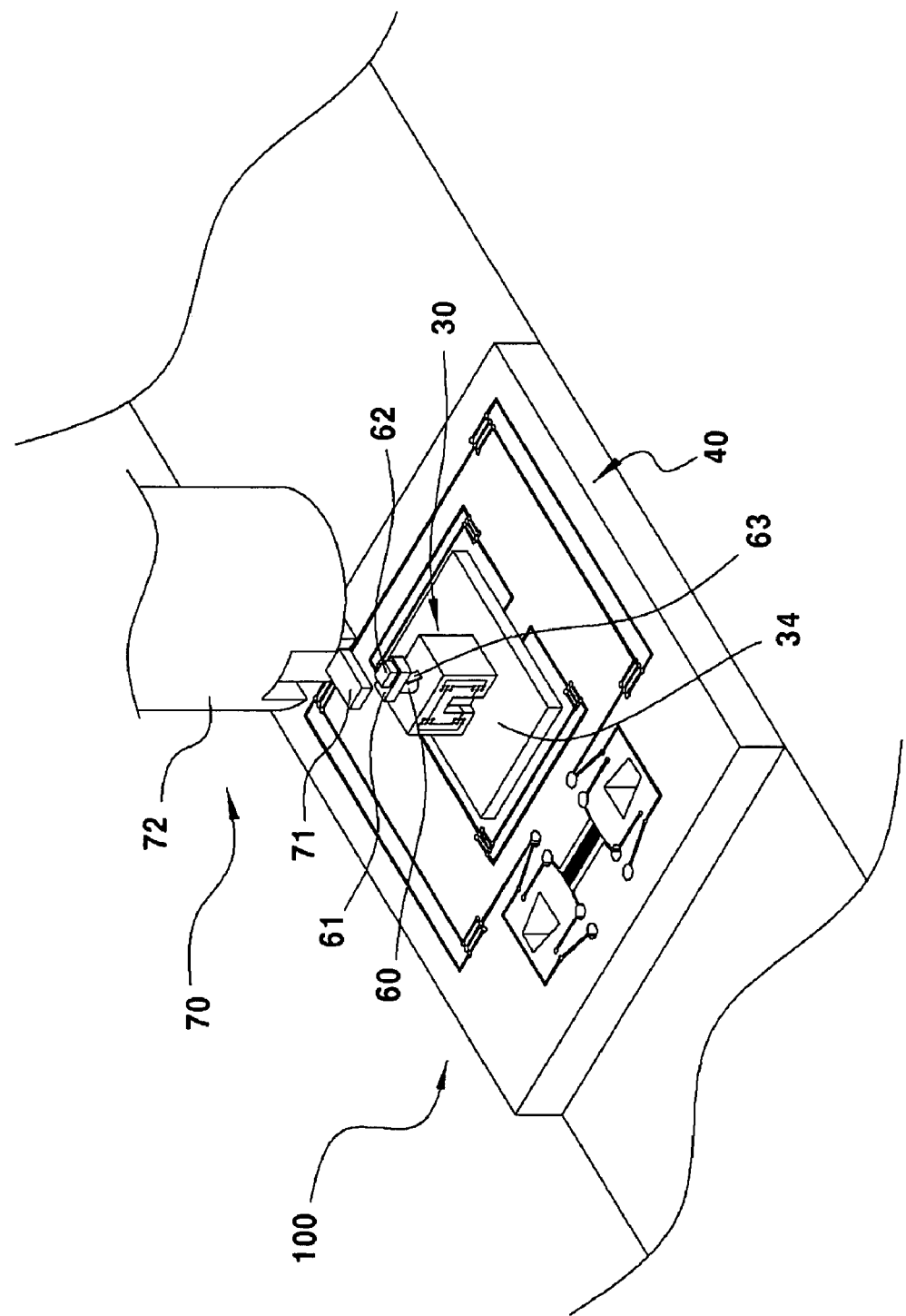
FIG. 8 is a perspective in part of an atom microscope provided with a 3-axis straight-line motion stage according to the invention.

FIG. 8 is a perspective in part of a sample test device provided with a 3-axis straight-line motion stage according to the invention. The sample test device comprises a 3-axis straight-line motion stage 100 supporting the sample, and an atom microscope inspecting the sample.

Here, the 3-axis straight-line motion stage 100 further comprises a sample support 60 positioned in a support receiving part 32 of a Z-line driving part as shown in FIG. 4C, a sample fixing part 61, which the sample 62 is placed on, attached to the end of the sample support 60, and a mirror 63 placed in parallel to the sample support and in inclined status under the sample fixing part 61.

The atom microscope 70 comprises a tip 71 scanning the sample 62, and a fixing base 72 to which the tip 71 is fixed.

Therefore, the sample may be precisely scanned by the operation of the 3-axis straight-line motion stage with the tip 71 positioned over the sample 62. At this time, the movement of the sample is detected by analyzing a laser beam projected to the mirror 63 and reflected from the mirror 63.

Now, specifically, the operating method of the respective elements of the 3-axis straight-line motion stage according to the invention will be given in detail herein below.

Referring to FIG. 4A, the X-axis stage 10 pushes the pressing parts 14-1, 14-2 outwardly if the piezoelectric element 13 is expanded, and then the first and second X amplifying parts 12-1, 12-2 are contracted in the direction perpendicular to the increasing direction of the length of the piezoelectric element 13 with a distance between the pressing parts 14-1, 14-2 widening (See FIGS. 6A and 6B). If the first and second X amplifying parts 12-1, 12-2 are contracted, the second X end 16-2 and the third X area 17 adjacent to the parts 12-1, 12-2 are straightly shifted to the first X end 16-1.

Meanwhile, if the piezoelectric element 13 is contracted, the first and second X amplifying parts 12-1, 12-2 are expanded, and then the second X end 16-2 and the third X area 17 adjacent to the parts 12-1, 12-2 are straightly shifted to the direction becoming more distant from the first X end 16-1.

Therefore, the third X area 17 is straightly shifted in the direction of the X-axis according to the contraction and expansion of the piezoelectric element 13.

In the Y-axis stage 20 shown in FIG. 4B, like the operation of the X-axis stage, if the piezoelectric element 23 is expanded, the first and second Y amplifying parts 22-1, 22-2 are contracted, and then the second Y end 26 and the second Y area RY2 adjacent to the end 26 are straightly shifted in parallel to the Y-axis toward the direction of the first Y end 25, whereas, if the piezoelectric element 23 is contracted, the first and second Y amplifying parts 22-1, 22-2 are expanded, and then the second Y end 26 and the second Y area RY2 adjacent to the end 26 are straightly shifted in parallel to the Y-axis in the direction becoming more distant from the first Y end 25.

Therefore, the second Y area RY2 is straightly shifted in the direction of the Y-axis according to the contraction and expansion of the piezoelectric element 23.

Since the Z-axis stage 30 shown in FIGS. 3 and 4C is fixed to the second Y area RY2 of the Y-axis stage 20, the stage 30 is shifted to the directions of the X-axis and the Y-axis according to the operation of the X-axis and Y-axis stages 10, 20. On the other hand, the Z-line driving part 31 of the Z-axis stage 30 is expanded or contracted from the side of the bottom part 34 to the direction of the Z-axis according to the contraction and expansion of the piezoelectric element 33. Therefore, according to the contraction and expansion of the Z-line driving part 31, the support receiving part 32 also is straightly shifted in the direction of the Z-axis.

Accordingly, since the X-axis, Y-axis, and Z-axis stages 10, 20, 30 are moved independently without mutual interference, they are able to shift the shifting area thereof exactly and precisely about the direction of the axis thereof.

The double complex springs adopted in the embodiment of the invention are embodied as four narrowing parts and two intermediate rods. Therefore, the total modulus of elasticity of the double complex springs is small; thereby a sufficiently large displacement may be generated even with a small driving force.

Further, a plurality of narrowing parts connected in series is arranged in parallel and in multiple rows to generate only straight-line motion. Specifically, although the narrowing parts forming a line in series may generate the displacement by their elastic transformation toward the serial direction, since the displacement of the direction perpendicular to the serial direction is hard to generate, the double complex springs have the degree of freedom for moving in only one direction.

Since, in the embodiment of the invention, the pressing part and the intermediate rod of the amplifying part are symmetrically arranged about the respective axis, other constitutional elements connected with the amplifying parts go through exactly the straight-line motion when the amplifying part is operated.

If the stage is driven in the vicinity of a resonance frequency thereof or beyond that, the stage is damaged due to a resonance, and is hard to control. If the resonance frequency of the stage is low, a velocity for driving the stage may not become high. Thus, in order that the stage is driven fast, preferably, the resonance frequency of the stage should be high.

Generally, a resonance frequency of a predetermined system is obtained from the following equation: $\omega=(k/m)^{1/2}$, where $\omega$=a resonance frequency, k=the modulus of elasticity, and m=mass.

Therefore, in order to increase the resonance frequency thereof in the stage of the invention, the mass should be small. To do this, the weight of the X-axis stage is reduced by forming holes 18-1, 18-2 having a predetermined size in the first and second X-axis amplifying parts 12-1, 12-2. Simultaneously, the intermediate rod portions 15-1A, 15-1B are formed as a trapezoid so that the mass thereof is maintained constantly. Thus, in the stage of the invention, the modulus of elasticity becomes higher, and thereby the resonance frequency also becomes higher.

Meanwhile, since the tip of the prior atom microscope scans a sample over the sample, the position for scanning the sample by the tip and the position for measuring the sample by a detector coincide with each other, and thereby the prior atom microscope generates a measurement error of Abbe.

However, according to the 3-axis straight-line motion stage of the invention, the detector of the atom microscope is equipped under the sample fixing part fixing the sample, and the tip scans the sample over the sample. Thus, according to the 3-axis straight-line motion stage of the invention, since the measuring position of sample by the detector and the scanning position by the tip coincide, the sample is measured exactly and precisely by the atom microscope without the measurement error of Abbe.

According to the 3-axis straight-line motion stage of the invention, since the X-axis stage 10 and the Y-axis stage 20 are designed to move on the coplanar surface, a point of action for a force and a center of weight for the respective stages are positioned on the coplanar surface, and thereby the moment is not generated and the vibration is generated relatively small. Thus, according to the 3-axis straight-line motion stage of the invention, the sample is moved exactly and precisely in the straight direction.

Further, since the X-axis stage 10 moved in the direction of the X-axis only does not interfere with the motion of the Y-axis stage 20, the motions of the stages 10, 20 are accomplished independently without a correlation. For example, since the motion of the X-axis stage does not comprise the error of the Y-axis motion by the Y-axis stage, the sample is moved exactly in the direction of the X-axis only. Further, the contrary case also is the same.

Although, in the embodiment of the invention, the Z-axis stage does not comprise the amplifying part, the amplifying part may be mounted on the Z-axis stage if the system needs a large displacement in the direction of the Z-axis.

Further, although, in the embodiment of the invention, the amplifying part is comprised in the X-axis and Y-axis stages, the amplifying part may be omitted.

Although, in the preferred embodiment of the invention, the amplifying part for amplifying the motion of the stage is used, the invention is not limited thereto, and the respective amplifying part may be transformed into the structure for decreasing the displacement by arranging the amplifying part to be rotated by 90°.

Although, in the preferred embodiment of the invention, the inside of the amplifying part is embodied as a frame structure having a vacant space to raise the resonance frequency, the invention is not limited thereto, and the structure removing a predetermined part of the third X area 17 of the X-axis stage and the second Y area RY2 of the Y-axis stage except for the amplifying structure may be embodied.

Although, in the preferred embodiment of the invention, a flexible complex hinge structure is used on one side of the stage, a flexible structure, such as a plate spring for generating a complete straight-line motion, may be adopted.

Although, in the preferred embodiment of the invention, the intermediate rod having a shape of a straight line or a trapezoid is adopted, the shape of a triangle or a lozenge may be adopted to raise the resonance frequency.

Although, in the preferred embodiment of the invention, the example that the 3-axis straight-line motion stage is applied to the atom microscope is described, the stage of the invention may be applied to a device for requiring super precision driving, such as semiconductor equipment.

From the foregoing, according to a 3-axis straight-line motion stage and a test device using the same according to the preferred embodiment of invention, since the X-axis stage and the Y-axis stage are independently displaced from each other, the motions of the stages are not interfered mutually, and since the degree of freedom of the respective stage is limited in only one direction by the flexible complex hinge structure formed in the stage, the sample is moved in a straight line exactly.

Further, since the amplifying part of the invention uses a symmetrical amplifying structure in order to amplify the range of motion by the piezoelectric element, the range of motion thereof is wider, and simultaneously, the motion is maintained exactly in the perpendicular direction.

Further, since the pressing part of the driving part in the respective stage has a frame structure, and the structure of the intermediate rod has a shape of a trapezoid, the resonance frequency of the stage is higher, and thereby the driving velocity of the stage is higher.

According to the atom microscope adopting the 3-axis straight-line motion stage of the invention, since the detector measures the position of the sample under the sample fixing part, the scanning position of the tip and the measuring position of the detector are coincided, and thereby the sample is measured precisely and exactly without the measurement error of Abbe.

What is claimed is:

1. A 3-axis straight line motion stage comprising:
a bottom plate having a predetermined area and thickness;
an X-axis stage fixed in a reference area of the bottom plate for moving in the direction of the X-axis, a first X area positioned from the reference area to the direction of the X-axis;
a Y-axis stage, positioned within the first X area and fixed in a second X area, which is located within the first X area for moving in the direction of the Y-axis a second Y area positioned from the second X area to the direction of the Y-axis; and
a Z-axis stage fixed in the second Y area, which is located within the first Y area and supports a predetermined sample for moving the sample in the direction of the Z-axis;
the X-axis stage comprising:
a piezoelectric element having a predetermined length, the length being changed in the direction of the Y-axis according to an input voltage;
and a first X driving part and a second X driving part connected to both ends of a longitudinal direction of the piezoelectric element, respectively, for moving in the X-axis direction a second X end within the first X area from a first X end within the reference area in the center of the piezoelectric element according to driving of the piezoelectric element,
wherein the X-axis, the Y-axis and the Z-axis indicate axes of rectangular coordinates, respectively.

2. The stage according to claim 1, wherein the first and second X driving parts comprise first and second X amplifying parts amplifying a displacement generated according to the driving of the piezoelectric element, and moving third and fourth X ends formed on a side opposite to side of the first X end in the center of the piezoelectric element, in the direction of the X-axis by the amplified displacement,
first and second X-line motion parts shifted in parallel in the direction of the X-axis by the amplified displacement,
first and second slits connecting the third and fourth X ends to first ends of the first and second X-line motion parts, respectively, and
a third slit connecting a second end opposite to the first end of the first X-line motion part, which is connected to the third X end, a second end opposite to the first end of the second X-line motion part, which is connected to the fourth X end.

3. The stage according to claim 2, wherein the first and second X amplifying parts comprise first and second pressing parts receiving the displacement of the piezoelectric element, intermediate rods formed in the longitudinal direction of the piezoelectric element towards both sides of the first and second pressing part in the center of the respective first and second pressing parts, and fourth and fifth slits connecting the intermediate rods each other, respectively.

4. The stage according to claim 3, wherein the intermediate rod comprises a post part formed to have a predetermined width, and a narrowing part having a thickness relatively thinner than the width of the post part by a semicircular groove having a predetermined radius in both ends of the post part.

5. The stage according to claim 4, wherein the respective first and second X amplifying parts further comprise a hole of a predetermined magnitude in the area surrounded by the fourth and fifth slits, the first pressing part and the intermediate rod.

6. The stage according to claim 5, wherein the first and second X-line motion parts comprise first and second X double springs connected to the third and fourth X ends through the first and second slits, and the third and fourth X double springs connected to the first and second X double springs through a pair of slits having a predetermined length and formed in the parallel direction about the X axis, the ends of the third and fourth X double springs being connected to each other through the third slit.

7. The stage according to claim 6, wherein the respective first to fourth X double springs comprise two intermediate rods arranged doubly, the respective intermediate rods comprise a post part having a predetermined width, and a narrowing part having a thickness relatively narrower than the width of the post part by a semicircular groove having a predetermined radius in both ends of the post part.

8. The stage according to claim 2, wherein the first and second X-line motion parts comprise first and second X double springs connected to the third and fourth X ends through the first and second slits, and third and fourth X double springs connected to the first and second X double springs through a pair of slits having a predetermined length and formed in the parallel direction about the X axis, the ends of the third and fourth X double springs being connected to each other through the third slit.

9. The stage according to claim 8, wherein the respective first to fourth X double springs comprise two intermediate rods arranged doubly, the respective intermediate rods comprise a post part having a predetermined width, and a narrowing part having a thickness relatively narrower than the width of the post part by a semicircular groove having a predetermined radius in both ends of the post part.

10. The stage according to claim 1, wherein the Y-axis stage comprises a piezoelectric element having a predetermined length, the length being changed in the direction of the X-axis according to an input voltage, and a first Y driving part and a second Y driving part connected to both ends of a longitudinal direction of the piezoelectric element, respectively, and fixed to a first Y end of the second X area for moving a second Y end opposite to the first Y end in the Y-axis direction on the basis of the piezoelectric element.

11. The stage according to claim 10, wherein the Z-axis stage comprises a bottom part having a predetermined area and thickness and fixed within the second Y area of the Y-axis stage, a Z-line driving part moving in the direction of the Z-axis and formed integrally to the bottom plate in the vertical direction, which is the direction of the Z-axis, from the surface of the bottom plate, and a piezoelectric element mounted to have a decreased or increased length in the direction of the Z-axis in a space of a predetermined size, the space being a region to which the bottom part and the Z-line driving part are adjacent and formed in the Z-axis line driving part.

12. The stage according to claim 1, wherein the Z-axis stage comprises a bottom part having a predetermined area and thickness and fixed within the second Y area of the Y-axis stage, a Z-line driving part moving in the direction of the Z-axis and formed integrally to the bottom plate in the vertical direction, which is the direction of the Z-axis, from the surface of the bottom plate, and a piezoelectric element mounted to have a decreased or increased length in the direction of the Z-axis in a space of a predetermined size, the space being a region to which the bottom part and the Z-line driving part are adjacent and formed in the Z-line driving part.

13. The stage according to claim 1, wherein the Y-axis stage comprises a piezoelectric element having a predetermined length, the length being changed in the direction of the X-axis according to an input voltage, and a first Y driving part and a second Y driving part connected to both ends of a longitudinal direction of the piezoelectric element, respectively, and fixed to a first Y end of the second X area for moving a second Y end opposite to the first Y end in the Y-axis direction on the basis of the piezoelectric element.

14. The stage according to claim 13, wherein the first and second Y driving parts comprise first and second Y amplifying parts connected to both ends of a longitudinal direction of the piezoelectric element, respectively, for amplifying a displacement generated according to the driving of the piezoelectric element and for moving the second Y end in the direction of the Y-axis by the amplified displacement, and first ends of first and second Y-line motion parts connected to the first and second Y amplifying parts, respectively, through first and second slits traversing a part of the first Y end and shifted in parallel in the direction of the Y-axis by the amplified displacement, second ends opposite to the first ends of the first and second Y-line motion parts connected to the first and second amplifying parts being connected to each other by a third slit.

15. The stage according to claim 14, wherein the respective first and second Y amplifying parts comprise first and second pressing parts receiving the displacement of the piezoelectric element 23, and an intermediate rod formed in both sides of the first and second pressing parts symmetrically to the X-axis in the center of the respective first and second pressing parts, the intermediate rod comprising a post part having a predetermined width, and a narrowing part having a thickness relatively narrower than the width of the post part formed by a semicircular groove having a predetermined radius in both ends of the post part.

16. The stage according to claim 15, wherein the first and second Y-line motion parts comprise first and second Y double springs connected to the first and second Y ends through the first and second slits, and third and fourth Y double springs connected to the first and second Y double springs through a pair of slits having a predetermined length and formed in the parallel direction about the Y-axis, the ends of the third and fourth Y double springs being connected to each other through the third slit.

17. The stage according to claim 1, wherein the Z-axis stage comprises a bottom part having a predetermined area and thickness and fixed within the second Y area of the Y-axis stage, a Z-line driving part moving in the direction of the Z-axis and formed integrally to the bottom plate in the vertical direction, which is the direction of the Z-axis, from the surface of the bottom plate, and a piezoelectric element mounted to have a decreased or increased length in the direction of the Z-axis in a space of a predetermined size, the space being a region to which the bottom part and the Z-line driving part are adjacent and formed in the Z-line driving part.

18. The stage according to claim 17, wherein the Z-line driving part comprises first and second Z-axis motion parts moving a first Z end positioned in the direction of the Z-axis from the bottom part to the Z-axis on the basis of the piezoelectric element according to the driving of the piezoelectric element, wherein the respective first and second Z-axis motion parts include first and second Z double springs and third and fourth Z double springs arranged in the direction of the Z-axis, the ends of the first and third Z double springs being connected through a fourth slit.

19. A sample test device using a 3-axis straight line motion stage, the device comprising:
   a 3-axis straight line motion stage supporting a predetermined sample and shifting the sample independently, precisely and exactly in the direction of the X-axis, the Y-axis or the Z-axis; and
   an atom microscope provided with the 3-axis straight-line motion stage for measuring the location of the sample using a laser and for scanning the sample;
   the 3-axis straight line motion stage comprising:
   a bottom plate having predetermined area and thickness;
   an X-axis stage, fixed in a reference area of the bottom plate, for moving in the direction of X-axis a first X area positioned from the reference area to the direction of the X-axis;
   a Y-axis stage positioned within the first X area and fixed in a second X area, which is located within the first X area, for moving in the direction of the Y-axis a second Y area positioned from the second X area to the direction of the Y-axis; and
   a Z-axis stage fixed in the second Y area which is located within the first Y area and supports a predetermined sample for moving the sample in the direction of the Z-axis,
   the Y-axis stage comprising:
   a piezoelectric element having a predetermined length, the length being changed in the direction of the X-axis according to an input voltage, and a first Y driving part and a second Y driving part connected to both ends of a longitudinal direction of the piezoelectric element, respectively, and fixed to a first Y end of the second X area for moving a second Y end opposite to the first Y end in the Y-axis direction on the basis of the piezoelectric element, wherein, the X-axis, the Y-axis and the Z-axis indicate axes of rectangular coordinates, respectively.

20. The device according to claim 10, wherein the Z-axis stage comprises:

a bottom part having a predetermined area and thickness and fixed within the second Y area of the Y-axis stage, a Z-line driving part moving in the direction of the Z-axis and formed integrally to the bottom plate in the vertical direction, which is the direction of the Z-axis, from the surface of the bottom plate, and a piezoelectric element mounted to have a decreased or increased length in the direction of the Z-axis in a space of a predetermined size, the spacing being a region to which the bottom part and the Z-line driving part are adjacent and formed in the Z-line driving part.

* * * * *